United States Patent
Lenhardt

(10) Patent No.: US 6,394,969 B1
(45) Date of Patent: May 28, 2002

(54) TINNITIS MASKING AND SUPPRESSOR USING PULSED ULTRASOUND

(75) Inventor: Martin L. Lenhardt, Hayes, VA (US)

(73) Assignee: Sound Techniques Systems LLC, Arlington, VA (US)

(*) Notice: Subject to any disclaimer, the term of this patent is extended or adjusted under 35 U.S.C. 154(b) by 0 days.

(21) Appl. No.: 09/417,772

(22) Filed: Oct. 14, 1999

Related U.S. Application Data

(60) Provisional application No. 60/104,233, filed on Oct. 14, 1998.

(51) Int. Cl.[7] .................................................. A61N 7/00
(52) U.S. Cl. ............................................................. 601/2
(58) Field of Search ......................... 601/2, 3; 600/439

(56) References Cited

U.S. PATENT DOCUMENTS

| | | | |
|---|---|---|---|
| 4,222,393 A | 9/1980 | Hocks et al. ................ 128/746 |
| 4,226,248 A | 10/1980 | Manoli ........................ 128/773 |
| 4,757,807 A | * 7/1988 | Densert et al. |
| 4,759,070 A | 7/1988 | Voroba et al. ................. 381/60 |
| 4,982,434 A | 1/1991 | Lenhardt et al. ........... 381/68.3 |
| 4,984,579 A | 1/1991 | Burgert et al. .............. 128/747 |
| 5,024,612 A | 6/1991 | Van Den Honert et al. ... 604/36 |
| 5,167,236 A | 12/1992 | Junker ......................... 128/746 |
| 5,325,872 A | 7/1994 | Westermann ................ 128/897 |
| 5,403,262 A | 4/1995 | Gooch .......................... 600/28 |
| 5,628,330 A | 5/1997 | Upham ........................ 128/864 |
| 5,663,727 A | 9/1997 | Vokac .......................... 341/132 |
| 5,692,056 A | 11/1997 | Gardner ..................... 381/71.2 |
| 5,697,975 A | 12/1997 | Howard, III et al. ......... 623/10 |
| 5,752,924 A | * 5/1998 | Kaufman et al. |
| 5,788,656 A | * 8/1998 | Mino |
| 5,795,287 A | 8/1998 | Ball et al. ..................... 600/25 |
| 6,068,590 A | * 5/2000 | Brisken |
| 6,078,838 A | * 6/2000 | Rubinstein |

FOREIGN PATENT DOCUMENTS

| | | |
|---|---|---|
| EP | 0 912 074 A1 | 4/1999 |
| WO | WO 9600051 A1 * | 6/1994 |
| WO | WO 96/00051 | 1/1996 |

OTHER PUBLICATIONS

A. Lockwood et al., "The functional neuroanatomy of tinnitus", Neurology 50, Jan. 1998, pp. 115–120.

J. Rendell et al., "Low-powered ultrasound in the inhibition of tinnitus", British Society of Audiology, 1987, pp. 289–293.

G. Carrick et al., "Low-powered ultrasound in the treatment of tinnitus: a pilot study", British Society of Audiology, 1986, pp. 153–155.

J.M.R. Delgado et al., "Brain Modification By High Frequency Signals", Bioelectrical Repair and Growth, 1995, pp. 331–332.

Carrick et al. British Journal of Audiology 20: 153–155 (1986).

* cited by examiner

Primary Examiner—Marvin M. Lateef
Assistant Examiner—Runa Shah Qaderi

(57) ABSTRACT

A system and method for tinnitus masking. Ultrasound noise is provided to a head of a patient as a vibration by way of a transducer, to thereby stimulate the auditory cortex. Once stimulated, the auditory cortex will suppress tinnitus. The ultrasound noise may be provided as an ultrasound frequency tone or as a range of frequencies that have been multiplied with an audio frequency. Pulsed ultrasound is utilized for ultrasound noise in the MHz range.

23 Claims, 2 Drawing Sheets

TINNITIS MASKING AND SUPPRESSOR USING PULSED ULTRASOUND

This application claims priority of U.S. Provisional Application No. 60/104,233 filed in the United States Patent and Trademark Office on Oct. 14, 1998, the entirety of which is incorporated by reference.

BACKGROUND OF THE INVENTION

1. Field of the Invention

The present invention relates to a system and method for masking tinnitus. In particular, the present invention relates to a system and method for masking tinnitus using high frequency signals that affect the cortical auditory neurons in the brain.

2. Description of the Related Art

Tinnitus is defined as any ringing in the ears for which there is no external source. For example, a ringing, buzzing, whistling, or roaring sound may be heard as a result of tinnitus. Tinnitus can be continuous or intermittent, and in either case can be very irritating to one who has such an affliction.

Prior to the present invention, there has been no consistently effective way to counter, or mask, tinnitus. Most of the attempts to date have focused on masking the perceived sound. For example, U.S. Pat. No. 4,222,393, issued to Robert Hocks et al., describes a tinnitus masker that provides sounds in the range of from 1000 Hz to 5000 Hz, with a peak around 3000 or 4000 Hz. The patient is provided with sounds of varying pitch, one after another, so that the patient can identify the particular external sound having the same pitch as the tinnitus that the patient is experiencing. Once this is done, a power operated sound is applied to the ear of the patient, with that sound including a range of frequencies extending in a range above and below the perceived pitch.

U.S. Pat. No. 4,226,248, issued to Samir Manoli, describes a phonocephalographic device, which is used to passively, non-invasively monitor sounds from the surface and cavities of a patient's head and correlate these sounds with a person's electrocardiograph (ECG). A pair of insertable ear microphones of ample sensitivity are inserted into the patient's ears, where they detect sounds from the surface and cavities of the head. These signals are processed, with the processing including the filtering of these signals through a frequency analyzer, which is made up of four Butterworth filters with a variable center frequency of between 150 Hz and 1000 Hz. In addition, the output signals may be passed to a oscillator for display on an oscilloscope, and or may be displayed on a chart recorder. As such, this apparatus may be used to diagnose certain medical problems of the patient, including tinnitus.

U.S. Pat. No. 4,759,070, issued to Barry Voroba et al., describes a patient controlled master hearing aid. The device includes a hearing test module and an operator's and patient's console. Based on this testing apparatus, the patient can select electronic components to be employed in his or her hearing aid, which can be configured to address tinnitus. Testing and selection of a tinnitus masker are performed using a pseudo-random generator, which is connected to circuits through an analog switch. U.S. Pat. No. 4,984,579, issued to Paul Burgert et al., describes a portable apparatus for treating afflictions of the ear. The apparatus temporarily changes the pressure in the ear canal to alleviate Meniere's symptoms, such as hearing loss, vertigo, tinnitus, nausea, and aural fullness, in which the patient can facilitate immediate self-treatment.

U.S. Pat. No. 5,024,612, issued to van den Honert et al., describes an external ear canal pressure regulating device and tinnitus suppression device. This device uses an in-the-canal external ear pressure-regulating device to alter the pressure of the fluid within the external ear canal. The device includes an earplug with a bulbous portion, which contacts the wall of the external ear canal and creates a seal that seals the external ear canal interior from the ambient environment. The earplug is inserted into the ear canal, and the bulbous end is compressed. Fluid is passed outwardly into the ambient environment through a valve, creating negative pressure in the exterior ear canal, which pulls the eardrum out. This decreases the pressure in the inner ear space. Once the bulbous end is released, it re-expands. This process can be repeated until the desired pressure differential, or tinnitus relief, is achieved.

U.S. Pat. No. 5,167,236, issued to Franz Junker, describes a tinnitus masker having an electric circuit arranged in a housing and an earpiece which produces a sound spectrum that masks the tinnitus. The sound spectrum contains a line spectrum with a fundamental tone, with an adjustment range of the fundamental tone of from 0.125 kHz to 20 kHz.

U.S. Pat. No. 5,325,827, issued to Saren Westermann, describes a tinnitus masker which uses one or more signal generators, a controllable amplifier, one or two electroacoustic transducers for converting the electrical signals into acoustic signals, and a voltage source. The signal generators generate a continuously repeated, sinusoidal pure tone signal which slowly moves through the audio frequency range and whose cycle duration can be adjusted between 0.1 and 1000 seconds.

U.S. Pat. No. 5,403,262, issued to Timothy Gooch, describes a minimum energy tinnitus masker, which produces a masking signal with a selected center frequency, selected bandwidth, and selected volume. The bandwidth selector allows for four selections, ⅛, ½, 1 octave bandwidth, as well as broad bandwidth; and the center frequency selector is selectable in a range of between 500 and 16,000 Hz.

U.S. Pat. No. 5,628,330, issued to George Upham, describes an apparatus for treating people who are afflicted with tinnitus. This apparatus includes an inner metal shell that is fitted onto a patient's head. The inner metal shell is nestled with a larger outer shell of similar characteristics. The patient experiences relief from tinnitus by holding an open end of the apparatus against the afflicted ear. The inventor of the '330 patent believes that his apparatus may focus or somehow direct the "natural healing process" of the human body to the injured part of the inner ear and/or direct external healing to the injured part of the inner ear. See column 4, lines 1–6.

U.S. Pat. No. 5,697,975, issued to Matthew Howard III, et al., describes a human cerebral cortex neural prosthetic for tinnitus. Howard's device can be positioned in the brain so that electrical discharges can be accurately transmitted to geometrically dispersed locations in either a cortex or the thalamus, to allow a physician to physiologically test location and function of the neural prosthetic electrodes to reduce/eliminate the patient's tinnitus. In this regard, Howard's invention treats tinnitus in the brain, and not in the inner ear. In particular, Howard describes that the normal transduction of sound waves into electrical signals occurs in the cochlea, which is a part of the inner ear located within temporal bone. The cochlea is tonotopically organized, which means that different parts of the cochlea respond optimally to different tones. One end of the cochlea (base)

responds best to high frequency tones, while the other end (apex) responds best to low frequency tones. The cochlea converts the tones to electrical signals, which are then received by the cochlear nucleus in the brain. This converted information is passed from the cochlea into the brain stem by way of electrical signals carried along the acoustic nerve, and in particular, the cranial nerve VIII. As the acoustic nerve leaves the temporal bone and enters the skull cavity, it penetrates the brain stem and relays coded signals to the cochlear nucleus, which is also tonotopically organized. Through many fiber-tract interconnections and relays, sound signals are analyzed at sites throughout the brain stem and the thalamus, with the final signal analysis site being the auditory cortex situated in the temporal lobe of the brain.

U.S. Pat. No. 5,663,727, issued to Peter Vokac, describes a frequency response analyzer and shaping apparatus, and digital hearing enhancement apparatus. The device provides many of the characteristics of a complete fast fourier transform suitable for audio signals and other signals. Vokac's device customizes the frequency response for a particular patient, by providing an FFT'ed signal in an audible frequency range.

U.S. Pat. No. 5,692,056, issued to William Gardner, describes a method and apparatus for intracranial noise suppression. Vibrations from an instrument, as well as vibrations in the bone structure of the patient, are sensed and processed to generate canceling noise, which is then fed into the inner ear through vibrations on the head. Gardner's device also includes an equalizer and an automatic adaptive coupler.

Also, there is on the market an electrical tinnitus suppressor called "Theraband™". This is a battery powered headset that delivers amplitude modulated radio frequency waves to the subject. The carrier is about 60 kHz (possibly variable), with audio frequencies in the 200 Hz to 20,000 Hz range. The means of delivery is to the ear of the subject, where the sounds are received like any other sound. Theraband™ uses electrical energy capacitively coupled to the head via electrodes on mastoid.

All of the above-mentioned tinnitus maskers do not appear to fully mask tinnitus, since they do not appreciate the true reason why tinnitus occurs. In particular, these conventional tinnitus maskers/suppressors operate under the assumption that the tinnitus problem is in the inner ear, and they attempt to provide a solution that is based on this assumption.

SUMMARY OF THE INVENTION

The invention is directed to a tinnitus masker, which includes an ultrasound source configured to output at least one ultrasound frequency. The masker also includes a vibration unit connected to the ultrasound source and configured to convert the ultrasound frequency to a vibration. The vibration unit is coupled to a person who experiences tinnitus, thereby providing a stimulation of the brain of that person, which in turn causes tinnitus masking.

The invention is also directed to a method of masking tinnitus, which includes a step of providing ultrasound noise to a head of a patient.

The invention is further directed to a method of examining a patient in order to provide an ultrasound treatment for that patient. The method includes a step of providing a plurality of ultrasound frequency tones, in sequence, to the patient, to determine an optimum ultrasound frequency for the patient. The method also includes a step of providing a plurality of audible frequencies modulated by the determined optimum ultrasound frequency, so as to determine a particular audible frequency that is optimum for the patient with respect to ultrasound tinnitus masking.

BRIEF DESCRIPTION OF THE DRAWINGS

The above-mentioned object and advantages of the invention will become more fully apparent from the following detailed description when read in conjunction with the accompanying drawings, with like reference numerals indicating corresponding parts throughout, and wherein.

DETAILED DESCRIPTION OF THE PREFERRED EMBODIMENTS

Figure 1:
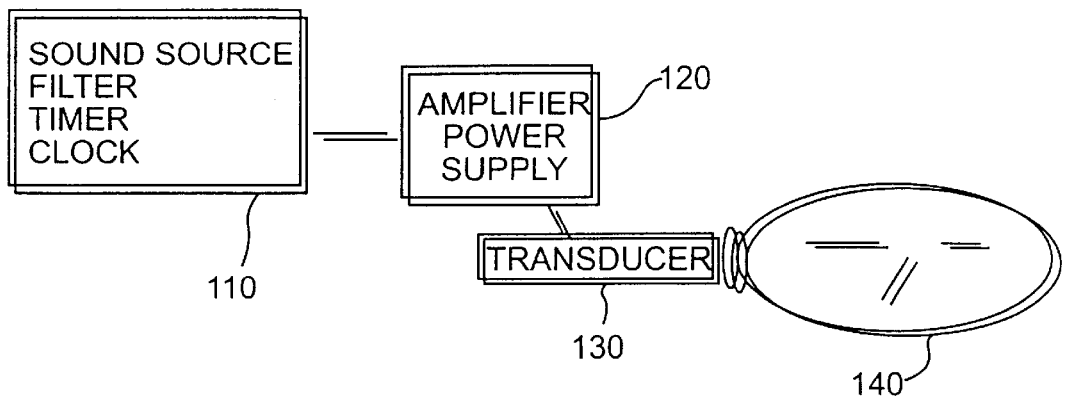
FIG. 1 is a block diagram of a tinnitus masker according to first and second embodiments of the invention.

The embodiments of the invention are directed to a method and a system for masking tinnitus, and may even suppress tinnitus. The incidence of tinnitus increases with age, affecting almost half of the population over seventy. Tinnitus is believed to exist in around 15% of the population. See 1989 National Strategic Research Plan, published by the National Institutes of Health, and referred to in U.S. Pat. No. 5,697,975, discussed in the Background section. Tinnitus is very often associated with hearing loss and noise exposure. Tinnitus can be described as a phantom sound (e.g., whistling, buzzing) that arises without any external stimulation. Often the source of tinnitus is assigned to the ear because it "sounds" like a sound, that it has the pitch, loudness and timbre of a sound. Tinnitus can be matched in quality to an external sound, and it is often associated with one ear or the other, or both ears. Tinnitus can often be masked by an external sound, as discussed in the Background section. There have been reports that, with the withdrawal of masking, tinnitus does not immediately reappear. This is termed tinnitus suppression. Suppression is typically short lived, and masking may again be required. The suppression phenomena is valuable in that masking may only be required for part of the day, such as for a short period of time in the morning, with the rest of the day being "tinnitus free" due to tinnitus suppression.

The fact that tinnitus is maskable suggests to most researchers that the source of tinnitus is in the ear to which it is localized. If this were true, then tinnitus masking would be nearly 100% effective using the method and apparatuses discussed in the Background section, which is not the case. In fact, the matching of tinnitus with an external sound can be very difficult and is often unreliable. This had lead some to refine the masking energy in both spectrum and intensity, so-called minimum level of masking.

Alternatively, there are some researchers that pose a central origin to tinnitus, with that central origin being beyond the ear and in the brain. For example, an article by Lockwood et al., published in 1998, found widespread activation of the primary cortex contralateral to the ear as being the source of tinnitus. In other words, the source of tinnitus is actually cortical and not in the ear. This is a reasonable view since it has been demonstrated that auditory cortical neuron reprogramming in the ear is not capable of providing frequency-specific stimulation. The reprogramming process may well produce tinnitus as a by-product. Perceptually, the source of cortical stimulation is directed to the peripheral sensory end organ. The reason for failure of attempts to mask or pharmaceutically treat tinnitus in the ear may well be that the ear is not the site of tinnitus!

This view of having a central origin for the source of tinnitus is supported by the lack of success with conventional tinnitus maskers, and also with the observations that after surgically severing the auditory nerve, tinnitus persists, and further with position emission tomography (PET) scans. The neural imaging data show that tinnitus activates the primary auditory cortex contralateral to the ear in which the tinnitus is localized, with that area activated being broader than that activated by sounds of similar frequency. This is one important reason why conventional tinnitus maskers fail, since they do not completely mask the tinnitus at the central origin or location. To broaden the frequency spread at the cortex, a masking signal that is broader and louder at the ear must be provided. However, when such a signal is given to patients who suffer from tinnitus, they find that the masker is more intolerable than the tinnitus. In other words, the cure is worse than the disease.

To determine a better cure for tinnitus, one has to understand the workings of the inner ear and the brain. External sounds activate both primary cortices, and each cortex is connected to a respective ear via a descending auditory nervous system. Maskers have an additional limitation in that if fitted on the left ear due to tinnitus localized left, both auditory cortices are stimulated, even though only the right cortex is activated by the tinnitus. The masker will in fact interfere with normal auditory function in the brain, and this will contribute to patient intolerance and discomfort. The brain will actively try to reduce the amount of masking arising up the auditory pathway by activating the descending auditory neural track. The result is that the brain will try to turn down the emasker, limiting its effectiveness.

As a result, what is needed is a stimulus that is sufficiently salient to mask the tinnitus, but is not treated as an unwanted signal that will be inhibited by the brain. A masker that provides such a stimulus will be effective in terms of auditory cortical activation, and will not interfere with everyday important sounds, such as speech. Such a masker will be effective with people having hearing loss.

While there may be disagreement about the site of tinnitus (ear versus brain), most researchers agree that tinnitus and hearing loss are linked. Although documentation is incomplete, some deaf individuals also complain of bothersome tinnitus. Conventional tinitus maskers are not very effective with those persons who have profound hearing loss. Also, it is desirable to have a masker that is audible only to the patient and does not radiate into the environment. Maskers that are implanted into the middle ear fit this criterion, but other types of maskers do not.

The masking stimulus that will meet all of the above criteria, and that is used in the tinnitus masker and method according to one embodiment of the invention, is ultrasonic noise. This noise can be made up of any part of the spectrum from 20,000 Hz up to 200,000 Hz. In a second embodiment, the noise band may extend from 10,000 Hz to 200,000 Hz, but it must be noted that the frequencies from 10,000 Hz to 20,000 Hz typically are not as effective in suppressing tinnitus as the higher frequencies. In a third embodiment, frequencies in an imaging frequency band of from 200,000 Hz to 5 MHz may be used with or without the other ranges in the first two embodiments.

There have been two reports of ultrasonic tinnitus suppression in the literature: Carrick et al., 1986 British Journal of Audiology, vol. 20, pages 153–155; and Rendell et al., 1987 British Journal of Audiology, vol. 21, pages 289–293. The Carrick article reported positive findings using a 500 kHz pulsed ultrasonic suppressor that produced 57 kPa of energy at 1 cm with 4 mW cm$^2$ of power. The Rendell article failed to replicate those findings using the same equipment and drawing subjects from the same clinic population. This technique appears to have been abandoned.

Pulsed ultrasound in the low to mid kHz has been shown to introduce lower frequency transients into the signal. It is now believed that the low frequency ultrasound that was effective in tinnitus suppression in the above-mentioned studies. Since this feature was not presented optimally or perhaps consistently, varied positive results could be expected, as is the case with the differences in results in the two studies.

In the case the MHz tonal or noise frequencies used according to the third embodiment of the invention, the stimulus is provided in a pulsed manner. The rate of pulsing is not critical, but a slow rate of pulsing, such as a rate from 1–10 Hz, is preferred. Because the tinnitus masker according to the embodiments of the invention is high pitched and broad in spectrum, the tinnitus-affected area of the cerebral cortex will virtually all be masked. Since the delivery intensity will be low, minimal energy (re: threshold) will be expended. Since ultrasound is difficult to detect by air conduction, the masker will be personal and inaudible to others who may be nearby the person undergoing tinnitus masking treatment. Since those with severe hearing loss can detect ultrasound, such as by using a supersonic bone conduction hearing aid as described in U.S. Pat. No. 4,982,434, which is incorporated in its entirety herein by reference, it will address their needs for a masker. Preliminary results suggest temporary tinnitus suppression by using an apparatus or method according to the embodiments of the invention.

The noise energy that is provided to suppress tinnitus of from 10 kHz upward can be a tone or filtered noise. It can be continuous or pulsed. The noise energy is preferably delivered near or at no more than 20 dB or so above threshold (e.g., between threshold and 20 dB above threshold). Delivery is preferably by a vibrator placed on the skin of the head or neck. A MHz pulser, to be used to deliver MHz noise signals according to the third embodiment, will preferably be delivered to the skin over the foreman magnum (back of skull by the neck). A transducer will preferably be similar to that used in transcranial Doppler insonation.

Figure 3:
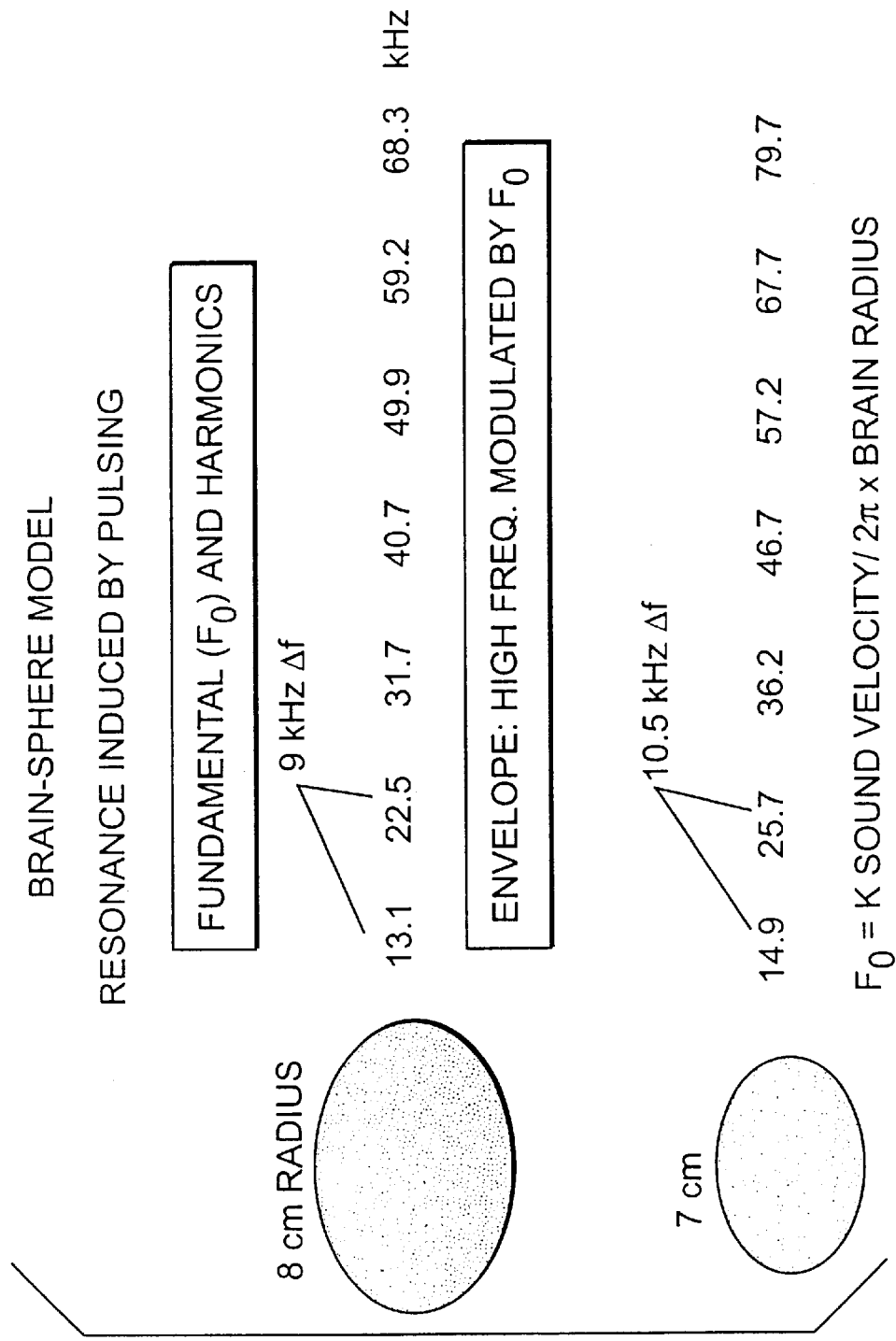
FIG. 3 is a diagram showing a brain-sphere model used to determine resonant frequencies of a brain.

Ultrasound affects not only a wide area in the ear (sending afferent information to the auditory cortex), but it also affects the brain itself. Ultrasound actually pulses the brain since the brain's fundamental resonant frequency is in the low ultrasonic range to the high audio range (determined by the diameter of the brain and sound velocity in water). FIG. 3 shows a brainsphere model used to compute the brain's fundamental resonant frequency for two differently-sized brains. The computation of the brain's fundamental resonant frequency is based on the model of the brain as a sphere with the skull as a boundary. As a result, a number of resonant frequencies will be generated when the brain is pulsed.

Pulsed ultrasound of noise according to the third embodiment will also send the brain into oscillation at its resonant frequency, and thus is also a viable means of stimulation. Delgado and Monteagudo (1995) demonstrated that low frequency amplitude-modulated (am) ultrasound can effectively stimulate cortical neutrons, which was used to stimulate brain tissues for brain modification. The present invention also stimulates cortical neurons, but for the purpose of tinnitus masking, which was not proposed by Delgado and Monteagudo.

Therefore, the embodiments of the present invention provide for the use of ultrasound to mask tintus by stimulating any remaining high frequency area in the ear and by suppressing tinnitus by acting on cortical auditory neurons in the brain.

FIG. 1 shows a block diagram of an apparatus for tinnitus masking according to either the first or second embodiments of the invention. In FIG. 1, a sound source unit 110 produces filtered noise (over a range of frequencies) or a frequency tone. In the first embodiment, the ultrasonic energy is presented as an amplitude modulated carrier that can be set at any discrete frequency from 20 kHz to 200 kHz. The range can be set to any discrete frequency from 10 kHz to 200 kHz in the second embodiment, and anywhere from 200 kHz to 5 MHz in the third embodiment. The carrier also may be swept over the entire range or part thereof. The carrier is multiplied by an audio tone in the range of from 1 kHz to 20 kHz. This corresponds to a carrier modulated by audio. The audio tone can also be presented over a small range or swept through the entire range of audio frequencies. Sweep time is variable, and preferably is set to a range of from 2 to 3 minutes. The flexibility in the carriers and audio frequencies allows a fitter to set frequency parameters such that the end product is stimulation over the ultrasonic range of from 20 kHz to at least 200 kHz. Speech also may be employed as part of the audio frequencies.

The preferred method of signal transmission is by way of double sideband modulation (suppressed carrier). Full amplitude modulation (full am carrier plus both sidebands) or single sideband modulation (either upper or lower sideband with the carrier and the other sideband suppressed) can alternatively be utilized. Modulation depth preferably does not exceed 90%, and the energy does not exceed 15 kPa (in water at 3.5 cm). Total power is preferably limited to 30 mW $cm^2$. Commercially available piezoelectric transducers are used to deliver the ultrasound in vibratory form to the patient's head. The precise level of energy (not to exceed 15 kPa) is to be determined for each patient during testing of each patient. The ultrasound may be audible during therapy.

Referring back to FIG. 1, the sound source unit 110 includes a filter for producing filtered noise, a timer, or clock. These elements operate as a pulse filter for ultrasonic noise, with the timer or clock providing the pulse timing. The output of the sound source unit 110 is provided to an amplifier and power supply unit 120, which amplifies the signal to the proper level to provide a signal to the patient at the low, minimal energy, as explained above. A transducer unit 130 converts the output of the power supply unit 120 to a vibration, which is felt by the patient. The transducer unit 130, preferably a piezoelectric device, is placed somewhere on the patient's head 140, preferably just behind the ear. Those vibrations are provided to the brain (not shown) within the skull of the patient's head 140, thereby stimulating the cortices and masking tinnitus.

Figure 2:
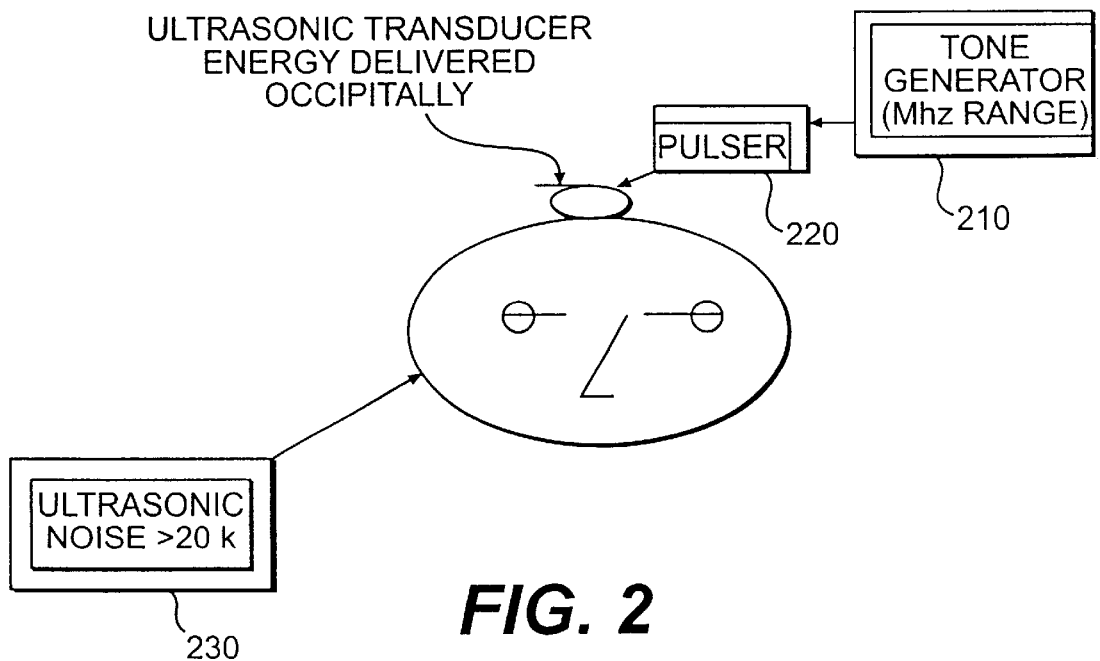
FIG. 2 is a block diagram of a tinnitus masker according to a third embodiment of the invention.

FIG. 2 shows the differences between the delivery of ultrasound noise according to the first and second embodiments as compared to the third embodiment. In the third embodiment, a tone generator 210 provides a tone in the MHz range. The output of the tone generator 210 is provided to a pulser 220, which provides pulses of MHz noise at a predetermined rate, say, between 1 and 10 Hz rate. A transducer (part of the ultrasonic noise unit 230) is preferably situated on the patient's skin on the back of the skull by the neck. FIG. 2 also shows the delivery of non-pulsed ultrasonic noise in the range of from 20 kHz to 200 kHz via an ultrasonic noise unit 230. In FIG. 2, ultrasonic noise unit 230 includes the sound source unit, amplifier and power supply unit, and transducer unit shown in FIG. 1.

Thus, according to the embodiments of the invention, an ultrasonic transducer delivers energy occipitally to the patient, to thereby mask and/or suppress tinnitus.

The ultrasound technique discussed herein is not without some disadvantages. The ultrasound technique does not produce low frequency stimulation of the inner ear, as with the conventional electrical maskers. Some tinnitus is low pitched, and thus may not be masked by the ultrasound technique described herein, but most tinnitus is not in this range. The electrical signal provided by the conventional tinnitus maskers is presumably demodulated at the skin or cochlea, leaving the audio frequencies "in" the inner ear. However, the ultrasound technique according to the embodiments of the invention does not appear to demodulate in the cochlea. Rather, the energy focuses at the base of the cochlea, in the region that codes audio frequencies from 5,000 Hz upwards.

However, the embodiments have several advantages over conventional maskers, some of which have already been described. Low frequency neural synchronization can be accomplished with ultrasound when it is amplitude modulated by very low audio frequencies, for example, 1 Hz to 50 Hz. The precept is of high pitch sound having a low frequency periodicity. The periodicity can be increased or decreased by changes in the audio frequency tone. Thus, the ultrasound tinnitus suppression apparatus and method according to the embodiments of the invention provides only high frequency stimulation presumably in the area of damage (as indicated by the tinnitus pitch). Furthermore, auditory nerve low frequency synchronous firing can also be incorporated in the ultrasound treatment regime according to the embodiments of the invention.

According to the invention, the site of action in the inner ear appears to be the hair cells for MHz amplitude modulation, in which the audio tone is reintroduced by demodulation. In the ultrasound method and apparatus according to the invention, demodulation does not appear to take place in the cochlea, but instead the site of action appears to take place at the cilia of the hair cells. The cilia have ultrasonic resonance, and a movement of endolymph by a compressive intracochlear ultrasonic wave may have rejuvenative effects on the cell directly. Stimulation of nearby cells (with respect to those injured) will also stimulate adjunct areas in the central nervous system, which could activate inhibitory influences in the ear.

While preferred embodiments have been described herein, modification of the described embodiments may become apparent to those of ordinary skill in the art, following the teachings of the invention, without departing from the scope of the invention as set forth in the appended claims.

What is claimed is:

1. A tinnitus suppressor and masker, comprising:
   an ultrasound source configured to output at least one ultrasound frequency;
   a pulser connected to the ultrasound source and configured to pulse the at least one ultrasound frequency to thereby provide at least one pulsed ultrasound frequency; and
   a vibration unit connected to the pulser and configured to convert the at least one pulsed ultrasound frequency to a vibration,
   wherein the vibration unit is adapted to be coupled proximate to a head of a person who experiences tinnitus in order to provide an ultrasonic vibration to a brain of the person to thereby suppress and mask the tinnitus.

2. The tinnitus suppressor and masker according to claim 1, further comprising an amplifier and power supply unit connected between the ultrasound unit and the vibration unit and configured to control an amplitude level of the at least one ultrasound frequency to be no more than 20 dB greater than a threshold level of sound for the person.

3. The tinnitus suppressor and masker according to claim 1, wherein the at least one ultrasound frequency is a frequency of between 20 KHz and 200 kHz.

4. The tinnitus suppressor and masker according to claim 3, wherein the at least one ultrasound frequency is swept over a range of frequencies centered at the at least one ultrasound frequency.

5. The tinnitus suppressor and masker according to claim 4, wherein a time to sweep the at least one ultrasound frequency over the range of frequencies is between 2 minute and 3 minutes.

6. The tinnitus suppressor and masker according to claim 1, wherein the at least one ultrasound frequency is a frequency of between 10 KHz and 200 kHz.

7. The tinnitus suppressor and masker according to claim 6, wherein the at least one ultrasound frequency is swept over a range of frequencies centered at the at least one ultrasound frequency.

8. The tinnitus suppressor and masker according to claim 1, wherein the at least one ultrasound frequency is a frequency of between 200 KHz and 5 MHz.

9. The tinnitus suppressor and masker according to claim 8, wherein the at least one ultrasound frequency is swept over a range of frequencies centered at the at least one ultrasound frequency.

10. The tinnitus suppressor and masker according to claim 1, wherein the at least one ultrasound frequency is a frequency of between 20 KHz and 5 MHz.

11. The tinnitus suppressor and masker according to claim 1, wherein the pulser pulses the at least one ultrasound frequency at a rate of between 1 Hz and 10 Hz.

12. The tinnitus suppressor and masker according to claim 1, wherein the ultrasound source is configured to modulate the at least one ultrasound frequency with an audio frequency in a range of from 1 Hz to 50 Hz, so as to create a modulated signal, with the at least one ultrasound frequency operating as a carrier frequency for the audio frequency, and
wherein the modulated signal is provided to the pulser, and
wherein a pulsed modulated signal is provided to the vibration unit.

13. A method of suppressing and masking tinnitus, comprising the steps of:
a) providing ultrasound noise by way of an ultrasound unit;
b) pulsing the ultrasound noise to thereby provide pulsed ultrasound noise; and
c) providing ultrasonic vibrations caused by the pulsed ultrasound noise, to a brain of a patient,
wherein the ultrasonic vibrations suppress and mask tinnitus for the patient.

14. The method according to claim 13, wherein the ultrasound noise is noise within a range of from 20 kHz to 200 kHz.

15. The method according to claim 13, wherein the ultrasound is noise within a range of from 10 kHz to 200 kHz.

16. The method according to claim 13, wherein the ultrasound is noise within a range of from 200 kHz to 5 MHz.

17. The method according to claim 13, wherein the pulsing step is performed at a rate of between 1 Hz and 10 Hz.

18. The method according to claim 13, wherein the ultrasound noise is swept over a range of frequencies in the providing step, and
wherein a time to sweep the ultrasound noise over the range of frequencies is between 2 minute and 3 minutes.

19. The method according to claim 13, further comprising:
a1) prior to step a), modulate the ultrasound noise with an audio frequency in a range of from 1 Hz to 50 Hz, so as to create a modulated signal, with the at least one ultrasound frequency operating as a carrier frequency for the audio frequency.

20. The tinnitus suppressor and masker according to claim 1, wherein the pulser pulses the brain of the patient at a resonant frequency of the brain, so as to cause the brain to resonate.

21. The method according to claim 13, wherein the pulsing step pulses a brain of the patient at a resonant frequency of the brain, so as to cause the brain to resonate.

22. A method of examining a patient in order to provide an ultrasound treatment for that patient so as to reduce tinnitus for the patient, comprising the steps of:
providing a plurality of pulsed ultrasound frequency tones, in sequence, to a head of the patient, to determine an optimum ultrasound frequency for the patient; and
providing a plurality of audible frequencies modulated by the determined optimum ultrasound frequency with the optimum ultrasound frequency operating as a carrier signal for the plurality of audible frequencies, so as to determine a particular audible frequency that is optimum for the patient with respect to ultrasound tinnitus suppressing and masking,
wherein the plurality of audible frequencies modulated by the determined optimum ultrasound frequency result in ultrasonic vibrations being provided to a brain of the patient, to thereby suppress and mask tinnitus.

23. The method according to claim 22, wherein the pulsed ultrasound frequency tones are provided to a head of the patient over a range of pulse rates, so as to determine a pulse rate that causes a brain of the patient to resonate at a resonant frequency of the brain.

* * * * *